US008922884B2

(12) United States Patent
Signaigo

(10) Patent No.: US 8,922,884 B2
(45) Date of Patent: Dec. 30, 2014

(54) FLEXIBLE OBJECTIVE LENS ASSEMBLY AND MICROSCOPE

(75) Inventor: Bryan T. Signaigo, Fenton, MO (US)

(73) Assignee: Global Surgical Corporation, St. Louis, MO (US)

( * ) Notice: Subject to any disclaimer, the term of this patent is extended or adjusted under 35 U.S.C. 154(b) by 787 days.

(21) Appl. No.: 12/899,963

(22) Filed: Oct. 7, 2010

(65) Prior Publication Data

US 2012/0087006 A1    Apr. 12, 2012

(51) Int. Cl.
*G02B 21/00* (2006.01)
*A61B 19/00* (2006.01)
*G02B 7/00* (2006.01)

(52) U.S. Cl.
CPC ............ *A61B 19/5223* (2013.01); *G02B 7/001* (2013.01); *G02B 21/0012* (2013.01)
USPC .......................................... 359/384; 359/368

(58) Field of Classification Search
USPC ......... 359/368, 389, 656, 821, 380, 381, 362, 359/372–374, 382, 384
See application file for complete search history.

(56) References Cited

U.S. PATENT DOCUMENTS

| | | | |
|---|---|---|---|
| 4,448,498 A | 5/1984 | Muller et al. ................. | 350/516 |
| 5,052,789 A | 10/1991 | Kleinberg ..................... | 359/375 |
| 5,288,043 A | 2/1994 | Tigliev ....................... | 248/123.1 |
| 5,312,393 A | 5/1994 | Mastel ............................. | 606/4 |
| 6,982,827 B2 | 1/2006 | Mora ............................. | 359/384 |
| 7,760,426 B2 * | 7/2010 | Hege et al. .................... | 359/384 |
| 2002/0014562 A1 | 2/2002 | Twisselmann ........... | 248/123.11 |

FOREIGN PATENT DOCUMENTS

| | | |
|---|---|---|
| DE | 3637311 A1 | 8/1987 |
| DE | 29707144 U1 | 8/1998 |
| DE | 29707144 U1 * | 8/1998 |

OTHER PUBLICATIONS

International Search Report and Written Opinion for corresponding PCT/US2011/054532 Date: Dec. 9, 2011 pp. 8.

* cited by examiner

*Primary Examiner* — Derek S Chapel
*Assistant Examiner* — Tamara Y Washington
(74) *Attorney, Agent, or Firm* — Michael L. Smith

(57) ABSTRACT

An objective lens assembly 316 to be attached to a surgical microscope includes an objective lens 328, a roll section 318, a pitch section 320, and an attachment mechanism 330. The roll section 318 allows the objective lens 328 to be rotated sideways without causing a pair of eyepieces 324 to move. The pitch section 320 allows the objective lens 328 to be rotated towards and away from the pair of eyepieces 324 without causing the pair of eyepieces to move. A surgical microscope 300 including the objective lens assembly 316 also includes a microscope body 308 and support structure 302, 304, 306, and 310.

39 Claims, 10 Drawing Sheets

US 8,922,884 B2

FLEXIBLE OBJECTIVE LENS ASSEMBLY AND MICROSCOPE

BACKGROUND

1. Field

The present disclosure is generally related to medical or surgical microscopes, and particularly microscopes that allow for the movement of the objective lens during use.

2. Description of the Related Art

In the field of surgical microscopes it is well known to provide support structure for mounting the microscope and positioning the microscope in a comfortable position for the user and to obtain the best available viewing angle of the field of interest. The support structure typically includes multiple support arms that pivot about various axes to allow the microscope to be moved rather freely in three-dimensional space. There are many types of procedures to be observed with the microscope, such as dental procedures or surgeries, and ophthalmic surgery, as well as many other types of medical procedures that benefit from the high magnification provided by a surgical microscope.

It can be important for the user to have the eyepieces placed at a comfortable level and position so that the user can maintain the position over a long time period without causing undo fatigue. However, during a procedure it is often desirable to move the objective lens to a new position so that another field of interest can be viewed. Most prior art microscopes would require the entire microscope to be repositioned and the user would also likely be required to move to a new position. This repositioning of the microscope and the user disrupts and extends the time of surgery.

One prior art patent for a Surgical Microscope, U.S. Pat. No. 6,982,827, assigned to Carl-Zeiss-Stiftung, discloses a microscope where the objective lens can be moved about one axis without requiring the eyepieces to be moved. The movement of the objective lens without also moving the eyepieces is limited to only one axis. In addition, the tubular portion or rotation ring that allows the movement of the objective lens independent of the movement of the eyepieces, significantly limits the amount of objective lens movement available in the one axis before the viewed area of interest begins to be clipped-off (commonly referred to as vignetting) and significant aberrations begin to be introduced to the viewed image. Also, it is often desirable to move the objective lens in more than one axis of space.

Another prior art patent for an Operation Microscope, U.S. Pat. No. 4,448,498, assigned to Carl-Ziess-Stiftung, discloses a microscope using a pair of Risley Prisms (wedge prisms), to allow the field of view of the microscope to move about a circular area by the simultaneous rotation of two wedge prisms with respect to each other. FIG. 1 illustrates the movement of a focal point of a Risley Prism pair, such as is disclosed in U.S. Pat. No. 4,448,498. The lines 10 represent one center and two peripheral field points within the field of view of the wedge prisms 12 and 14. The center of circle 16 will follow the circumference of circle 18 and is controlled by rotation of prism 14 (reference number 20 and its associated arrows illustrates this relationship). The center of the field of view of the combined wedge prisms 12 and 14 follows the circumference of circle 16 and is controlled by rotation of prism 12 (reference number 22 and its associated arrows illustrates this relationship). The center of the field of view of the Risley prism pair 12 and 14 may be positioned at any point with the area of circle 24 and is controlled by the combined rotational positions of prisms 12 and 14. This combined rotation becomes quite complicated when moving from one position to a next position and requires two simultaneous and often opposite rotations of prisms 12 and 14.

An example of the required prism rotations follows. If a starting position in the center of circle 24 is at coordinates 0,0 and prisms 12 and 14 each deviate a light beam 10 degrees, the prisms 12 and 14 will be 180 degrees out of phase with each other. In other words, at coordinate 0,0 the thickest edge of prism 12 will be at 12 o'clock, and the thickest edge of prism 14 will be at 6 o'clock. Starting from the 0,0 position in order to move the field of view to a 10, 0 position (that is 10 units to the right along the x-axis), prism 12 needs to rotate approximately 13 degrees clockwise and prism 14 needs to rotate approximately 13 degrees counter-clockwise. This requires, in a manual system, for the operator to perform two separate rotations, in opposite directions. The operator would also need to somehow know and monitor the amount of rotation made and the amount of rotation required by the prisms 12 and 14. The first example above may appear straight forward because each prism rotates the same amount though in opposite directions. However, starting from position 0,10 (that is 10 units up along the y-axis), movement becomes more complex. To place the field of view of the prism pair 12 and 14 at coordinate 0,10 requires prism 12 to be rotated to approximately −77 degrees (relative to the starting position at 0,0) and prism 14 to be rotated to approximately −103 degrees. Then to move to position 10, 10 (10 units along the x-axis and 10 units along the y-axis) requires rotating prism 12 to a position of approximately −26 degrees and prism 14 to a position of approximately −64 degrees. Because of the required complicated rotations of Risley prisms 12 and 14, such rotations are typically controlled by motors, gears, and some type of controller with programming to control the amount and relative rotation of prisms 12 and 14, to move the field of view to a desired location within circle 24 based on input from a user interface, such as a joystick or control pad. Such automation adds significant cost to a microscope and the need for a surgeon to keep track of the user interface. In addition, to the complexity and cost of a Risley prism pair system, the Risley prisms can introduce additional glare and the resolution of the observed field is degraded compared to other objective lenses. Also, the amount of change in the focal point (size of circle 24) is limited by the wedge thickness of prisms 12 and 14.

Therefore, a need exists for a surgical microscope that allows the objective lens to be moved by a user easily and with no distraction in both pitch and roll directions of rotation, and without requiring the user to move. It is also desirable to provide an assembly that allows existing microscopes to be upgraded to provide the enhanced objective lens movement.

BRIEF DESCRIPTION OF THE DRAWINGS

The drawings described are for illustration purposes only and are not intended to limit the scope of the present disclosure.

DETAILED DESCRIPTION OF THE PREFERRED EMBODIMENT

Example embodiments will now be described more fully with reference to the accompanying drawings.

Figure 1:
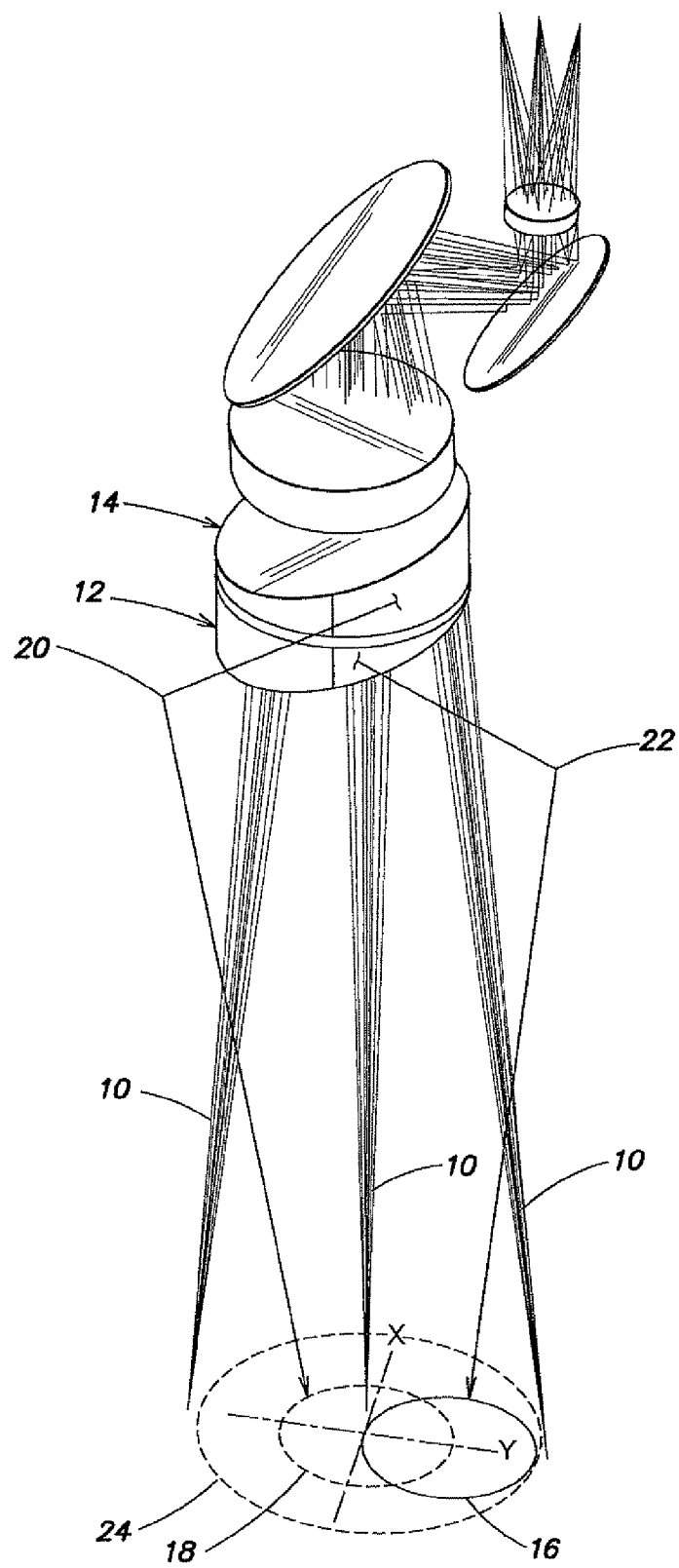
FIG. 1 is a perspective view of the optics of a prior art system.
Figure 2:
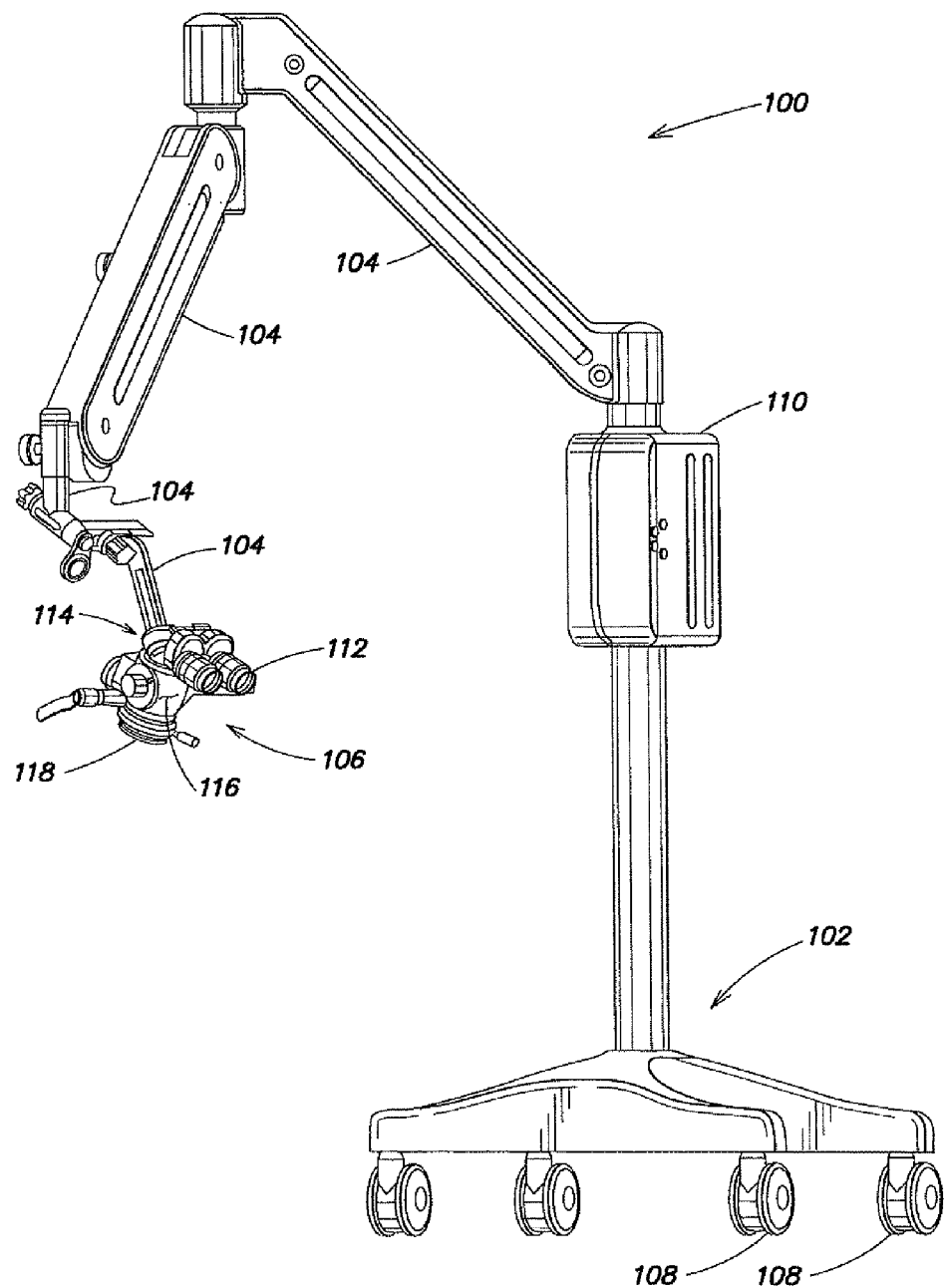
FIG. 2 is a perspective view of a prior art microscope.

FIG. 2 is an example of a prior art surgical microscope 100. Microscope 100 includes a base 102, support arms 104, and a microscope assembly 106. Microscope 100 may also include wheels 108 for moving the microscope 100 and a housing 110 that may contain control devices, power supplies, and light sources. Microscope assembly 106, as shown, includes binocular eyepieces 112, inclinable binocular assembly 114, microscope body assembly 116, and objective lens assembly 118. Instead of inclinable binocular assembly 114, microscope assembly 106 could include a fixed binocular assembly. The inclinable binocular assembly 114 is preferred because it allows the eyepieces to be rotated up and down to accommodate various viewing angles. One of the attachment arms 104 is pivotally attached to the microscope body assembly (at a location hidden in FIG. 2). If a user desires to move the objective lens assembly 118 to view a different field of interest, a user will be forced to move the entire microscope assembly 106 to accommodate the new objective lens position. This disrupts surgery and the concentration of the surgeon until a new comfortable and effective position is achieved. In addition, moving the entire assembly adds to the surgical time and possibly expense required compared to the inventive present example shown and described below.

Figure 3:
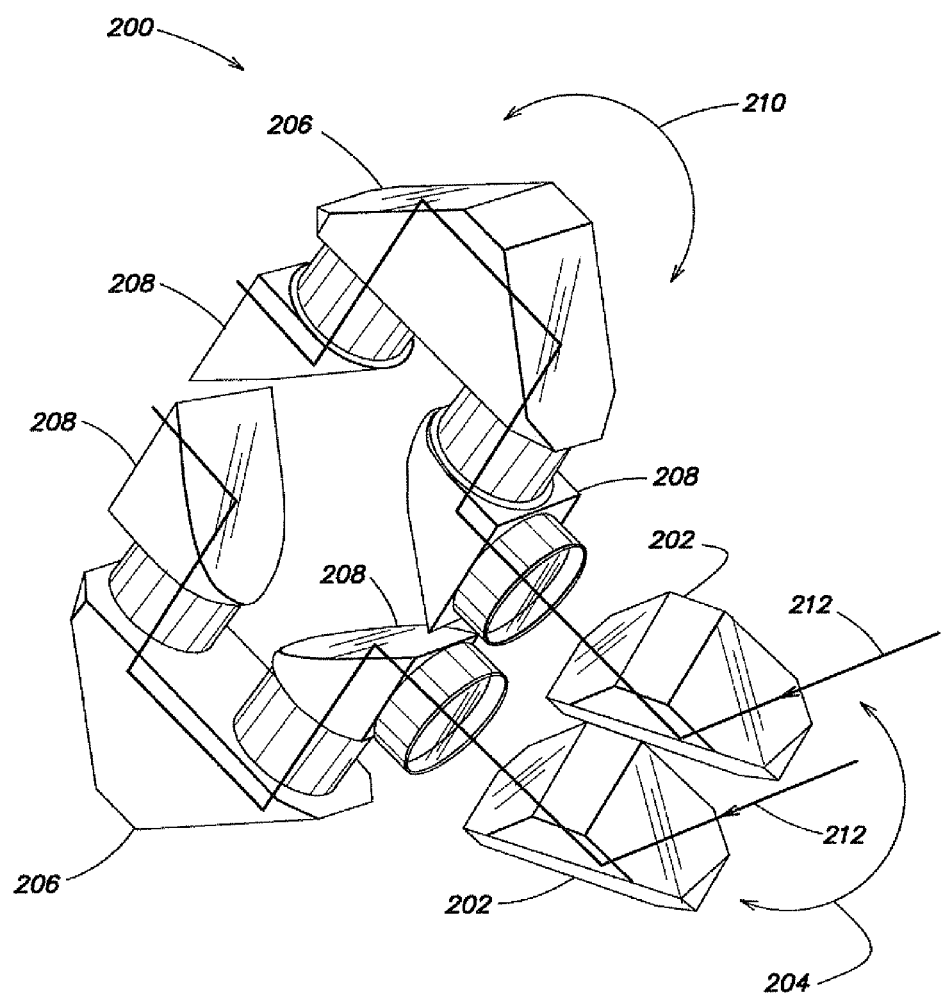
FIG. 3 is a perspective view of a prism assembly in accordance with one example of the present disclosure.

FIG. 3 is an example of a prism assembly 200 that allows an objective lens (not shown) to be moved in pitch and roll without moving the eyepieces (not shown) of a microscope in accordance with the present inventive example. FIG. 3 provides a visual representation of the manipulation of the light path without the clutter of all the mechanical structure surrounding the prisms. The roll prisms 202 allow an objective lens to rotate sideways, generally as indicated by arrows 204. The pitch prisms 206 and 208 allow the objective lens to rotate, generally as indicated by arrows 210. As will be described in detail below, the inventive examples permit the prisms 202 and 206 to be rotated independently of each other and independently of a pair of eyepieces. This independent rotation in pitch and roll allows a user to conveniently, with minimal surgical interruption, change the viewed field of interest, as indicated by light paths 212, without moving the pair of eyepieces. The objective lens assemblies, in accordance with the present invention, may be moved to the field of interest by a user simply grasping and moving the objective lens assembly in the direction of the field of interest. There is no need for complicated, expensive optics that increase costs while compromising image quality, as required by the prior art. There is also no need to readjust any associated microscope support arms or other structure to move the field of view while maintaining the eyepieces/viewing unit stationary. This allows the user/surgeon to avoid fatigue by enabling the surgeon to maintain a comfortable viewing position throughout surgery, even while moving the objective lens.

It is noted that the pitch and roll prisms could be realized using mirrors, instead of the shown prisms, a combination of prisms and mirrors, or any manner of manipulating the direction of the light path of the viewed field towards the eyepieces. The degree of travel in pitch and roll in the present inventive example is limited by the physical size of the prisms or mirrors used so that separate light paths 212 can be maintained. Preferably, the rotation of prisms 202 are stopped before vignetting begins. As one skilled in the art will realize, the pitch section of prisms 206 and 208 are essentially a type of inclinable binocular unit, such as are known in the prior art. The pitch section of the present inventive example may need to be modified from standard inclinable binocular units to accommodate coupling with an existing microscope body and the roll section.

Figure 4:
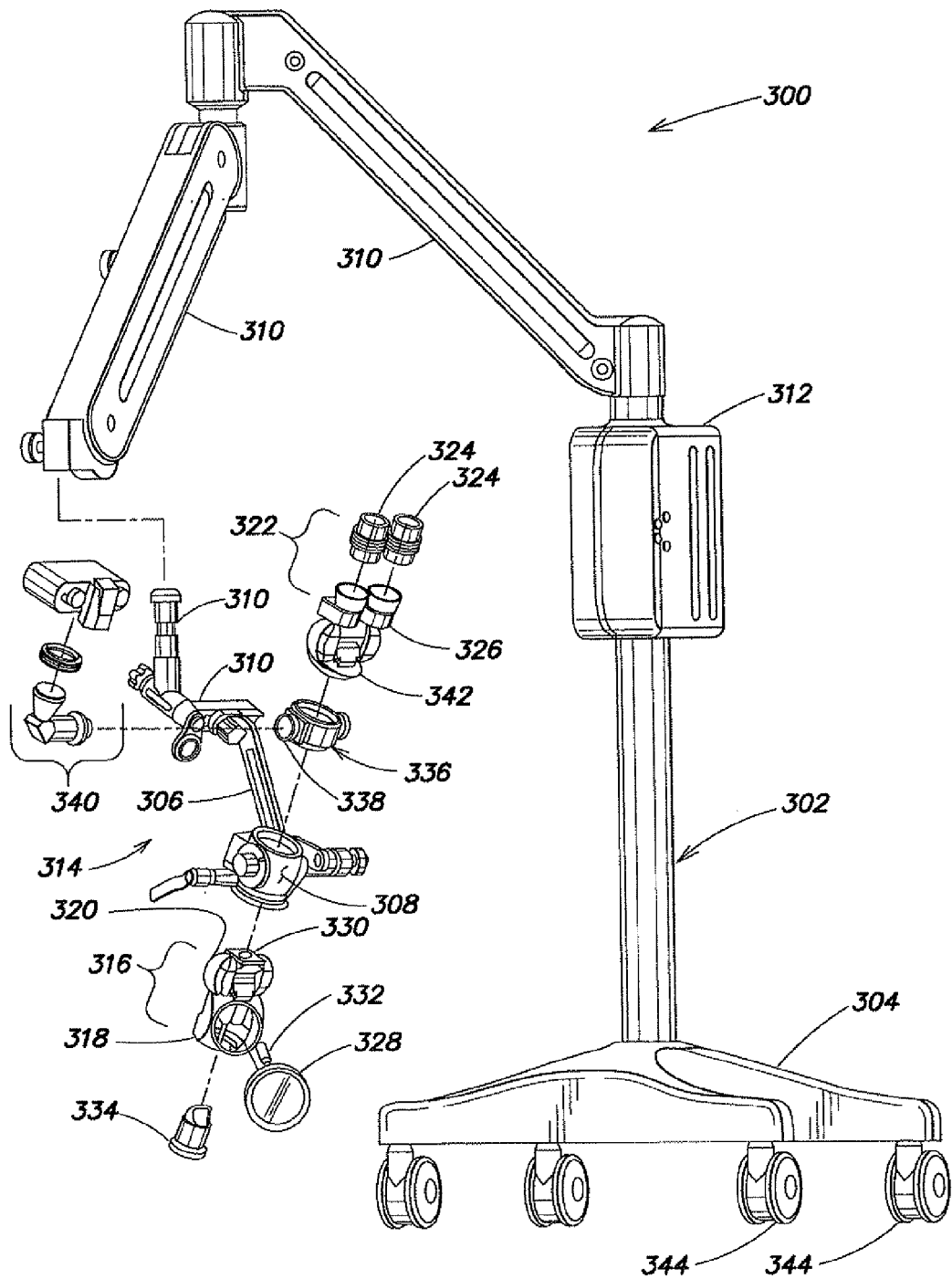
FIG. 4 is a perspective view with a partial exploded view of a surgical microscope in accordance with one example of the present disclosure.

FIG. 4 shows an example of a microscope 300, in accordance with the present invention. Microscope 300 preferably includes support structure 302 and 304 for supporting and positioning the microscope in a desired position. Microscope 300 also includes a support arm 306 pivotally connected to a microscope body 308, as well as other support arms 310 that are similar to arms 104 of FIG. 2. Housing 312 may also be similar to housing 110 of FIG. 2, and may include motors to cause the movement of various microscope portions. User interface devices such as foot-controllers, joysticks, mouth-controllers, keyboards, and touch screens are not shown for simplicity. A microscope assembly, shown generally at 314, is in accord with the present example. Microscope assembly 314 preferably includes microscope body 308, objective lens assembly 316 that includes a roll section 318 and a pitch section 320, a viewing unit 322 that includes a pair of eyepieces 324 and holders 326, an objective lens 328, and an attachment mechanism, shown as black box 330 at end of pitch section 320. Roll section 318 allows the objective lens 328 to be rotated in roll (roll is also referred to in the present example, as sideways rotation) directly by a user, without causing the viewing unit 322 to move. Pitch section 320 rotates about an axis perpendicular with respect to roll section 318, and allows the objective lens 328 to be rotated in pitch (pitch is also referred to in the present example, as rotating towards and away from the pair of eyepieces 324) directly by a user with respect to the viewing unit 322 without causing the pair of eyepieces 324 to move. The attachment mechanism 330 preferably includes structure for attachment to microscope body 308, including a mechanism that allows the objective lens assembly 316 to be retrofitted to existing microscopes. In this way, a microscope already purchased by a user can be upgraded to include the inventive objective lens assembly 316 without the need to purchase an entirely new microscope.

Objective lens assembly 316 preferably also includes a fine focus mechanism 332, similar to those known in the art. Objective lens assembly 316 also typically includes an illumination module 334, similar to those known in the art. Those skilled in the art will appreciate that the position of the roll and pitch sections 318 and 320 could be switched from that shown, so that the pitch section was attached to the objective lens 328 and the roll section attached to the microscope body 308, however a more complex optical and mechanical design would be required to maintain the optical path between the roll and pitch sections.

Microscope assembly 314 may also include a beam-splitter having a connector 338 for attaching additional optical recording device 340 or additional viewing units (not shown). Viewing unit 322 may additionally include an inclinable binocular unit 342 for allowing additional movement of the eyepieces without adjusting the support arms 306, 310. It is noted that because pitch section 320 provides essentially the same movement as inclinable binocular unit 342, as a user may be able to forgo the cost of binocular unit 342. Support structure 304 may be a wheeled base that includes wheels or casters 344 to allow microscope 300 to be easily moved. Microscope 300 could also be made to attach to a wall, ceiling, chair, bed, table, or other structure suitable for supporting a microscope and for placement to view a field of interest. Arms 306 and 310 are rotatable about different axes for initially positioning microscope 300.

Figure 5:
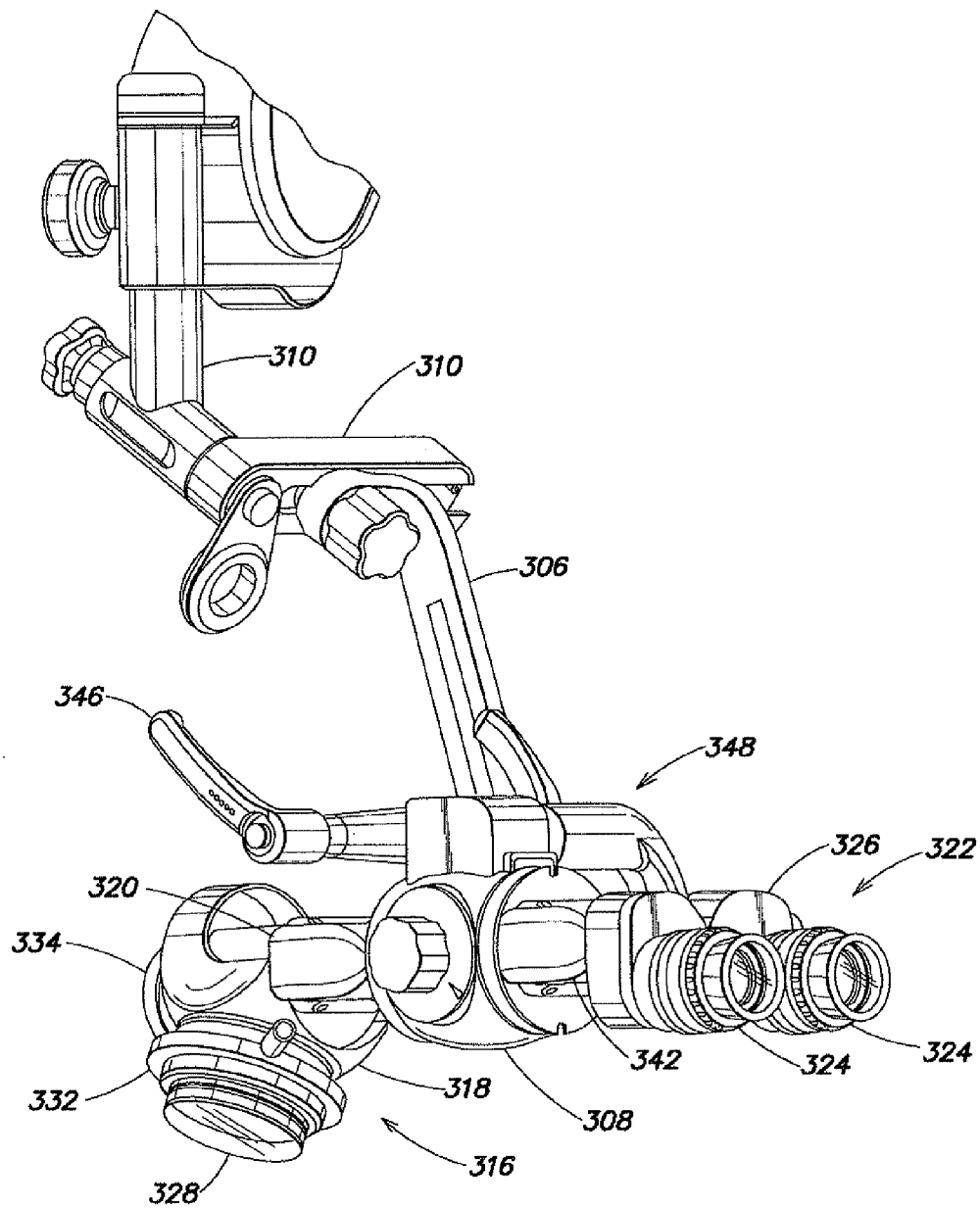
FIG. 5 is a non-exploded perspective view of a part of the exploded portion of FIG. 4.

FIG. 5 shows an assembled view of a part of the exploded portion of FIG. 4, including support arms 306 and 310. Arm 306 is pivotally attached at a location not seen to microscope body 308. The objective lens assembly 316 is shown attached to the body 308 on one side and viewing unit 322 is attached on an opposite side of body 308. The example of FIG. 5, shows viewing unit 322 with eyepieces 324 and holders 326, and inclinable binocular unit 342.

The roll section 318 rotates sideways with respect to the pitch section 320 and includes the pair of prisms 202 of FIG. 3, that rotate in unison for directing light towards eyepieces 324. The roll section 318 of FIG. 5 also shows objective lens 328, fine focus mechanism 332, and illumination module 334. The illumination module is typically connected to a light source or power source in housing 312 (see FIG. 4) via a fiber cable not shown.

The pitch section 320 allows the objective lens to be rotated towards and away from the pair of eyepieces 324 without causing the pair of eyepieces 324 to move. The prisms 206 and 208 of FIG. 3 are held within section 320, where prisms 208 rotate so that pitch section 320 rotates about an axis perpendicular with respect to the roll section 318. Handle 346 allows a user to pivot microscope assembly 348 with respect to arm 306. Microscope assembly 348 differs from assembly 314 in that the beam-splitter 336 and optical recording device 340 are not included.

Figure 6:
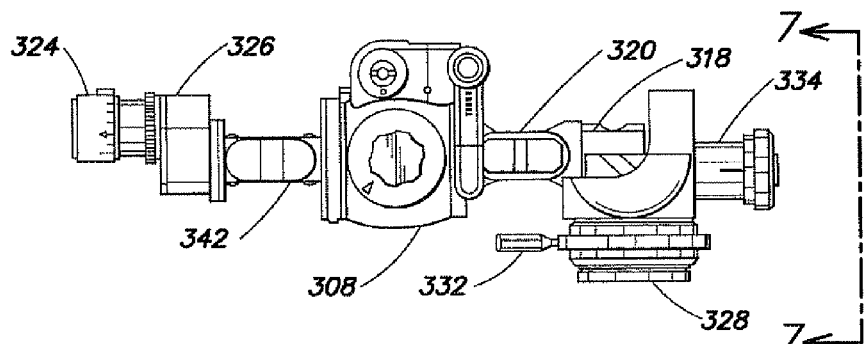
FIGS. 6, 6A, and 6B are side elevation views of an example of the present disclosure in different pitch positions.
Figure 6A:
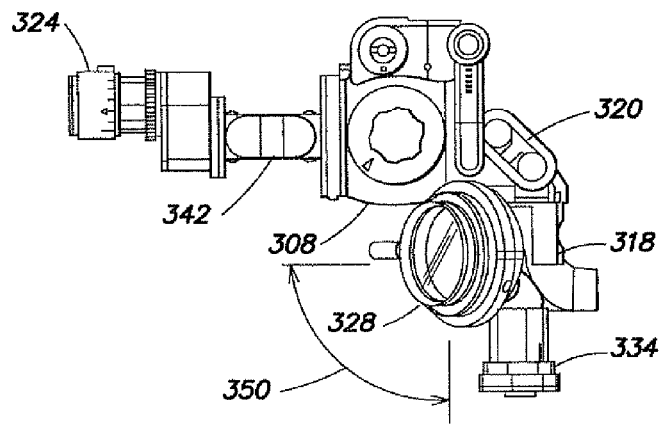
Figure 6B:
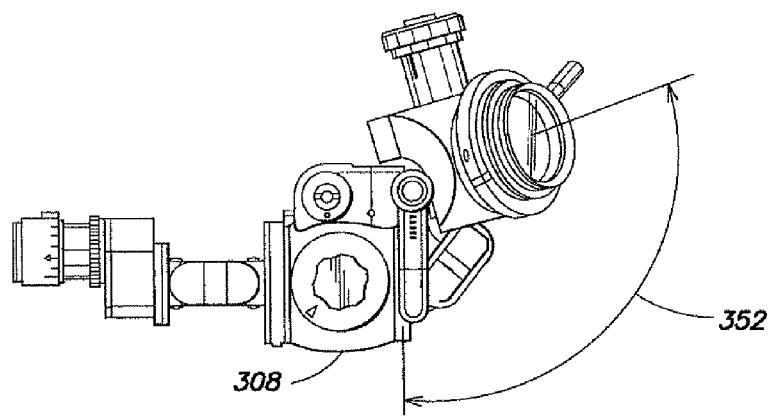

FIGS. 6, 6A, and 6B show a microscope assembly 348 in three different pitch positions. FIG. 6 shows assembly 348 in a fully extended, straight line where an image will be viewed through eyepieces 324 at a right angle to a field of interest viewed below objective lens 328. FIG. 6A shows pitch section 320 rotated to a maximum amount towards the eyepieces 324. Arrows 350 show the maximum amount of rotation of pitch section 320 towards the eyepieces 324. FIG. 6B shows pitch section 320 rotated to a maximum amount away from the eyepieces 324 with arrows 352 indicating the maximum amount of rotation. FIGS. 6A and 6B also show roll section 318 rotated with respect to FIG. 6.

Figure 7:
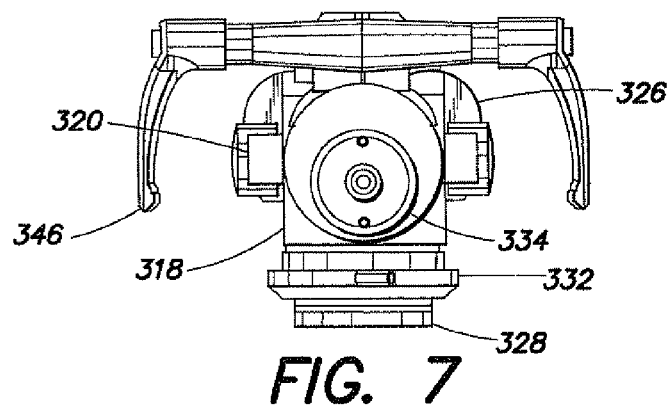
FIG. 7 is a front elevation view along line 7-7 of FIG. 6.
Figure 7A:
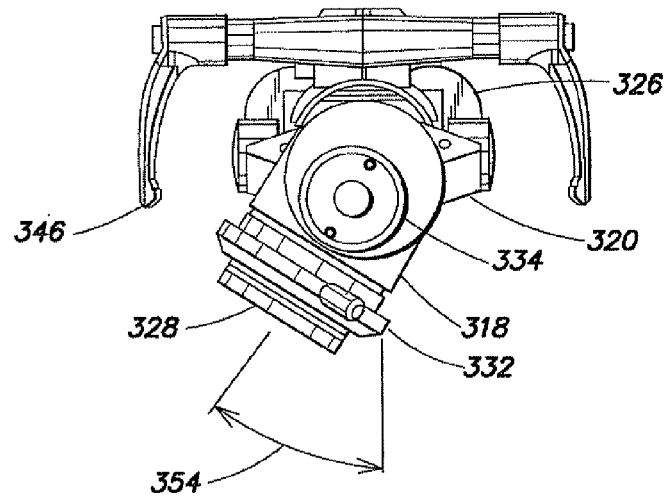
FIGS. 7A and 7B are front elevation views of an example of the present disclosure in different roll positions.
Figure 7B:
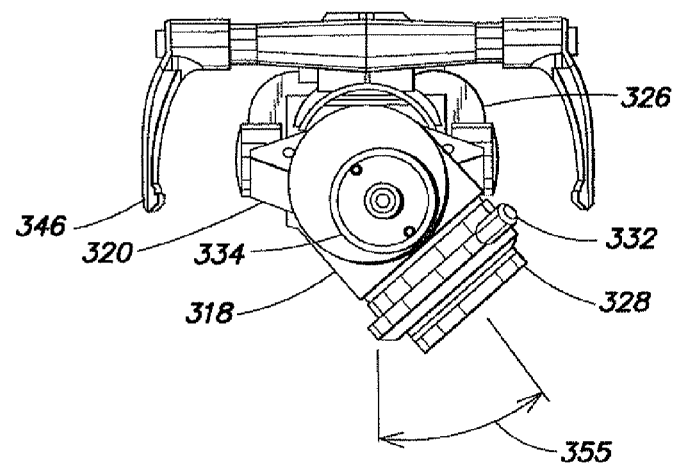

FIG. 7 is a front elevation view of FIG. 6 taken along line 7-7, and shows roll section 318 in a neutral position relative to any sideways rotation. FIG. 7A shows a full extent of right sideways rotation of the objective lens 328, as indicated by arrows 354. FIG. 7B shows a full extent of left sideways rotation of the objective lens 328, as indicated by arrows 355.

Figure 8:
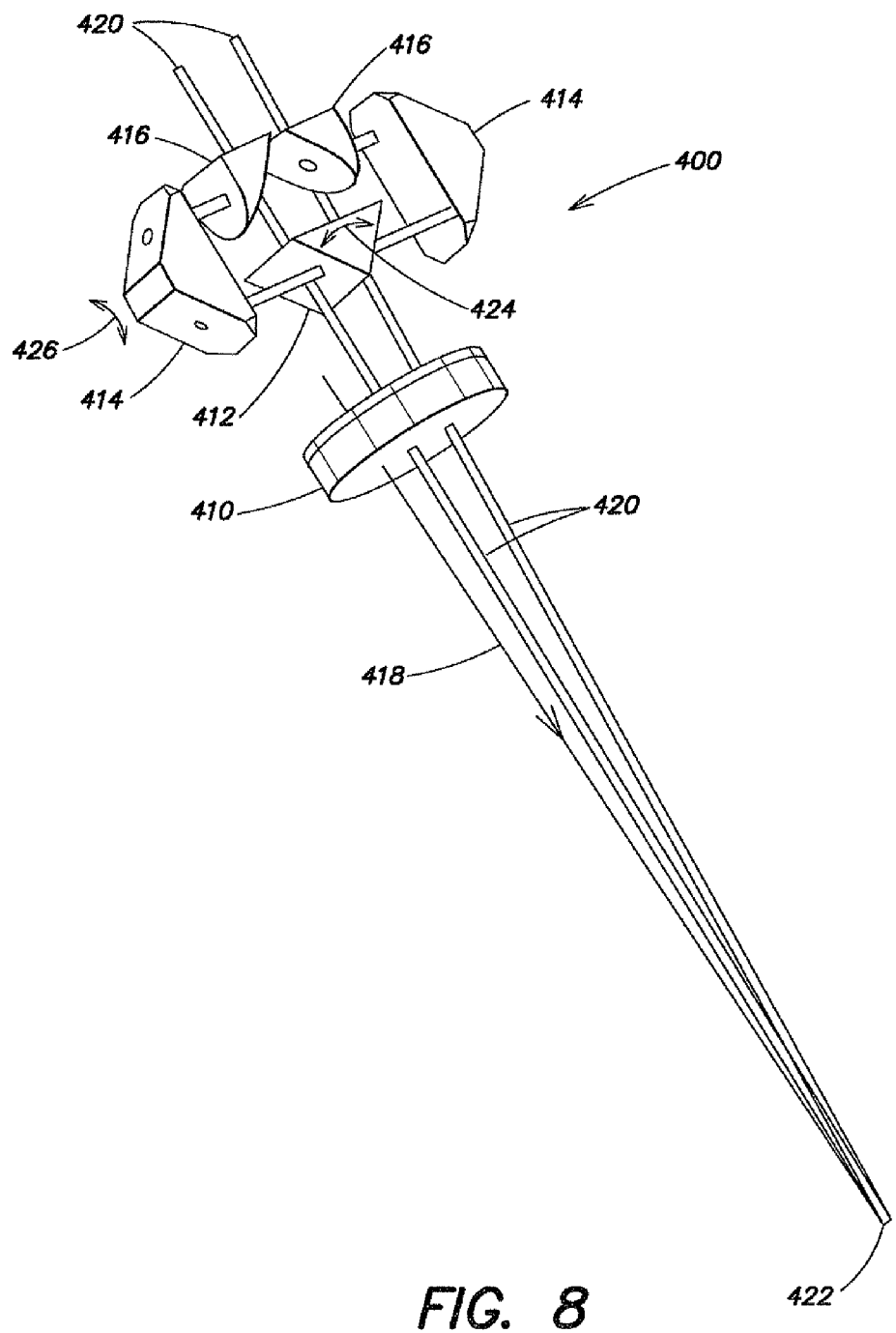
FIG. 8 is a perspective view of the optical components of another example of the present disclosure.

FIG. 8 is a perspective view of another example of an objective lens assembly 400, in accordance with the present example, showing only the main optical components for clarity. Assembly 400 includes objective lens 410, 90 degree mirror 412, Porro prisms 414, and right angle prisms 416. Line 418 represents light from an illumination module (not shown) and lines 420 represent the left and right beam paths of the field of view at point 422. The example of FIG. 8 is more compact than the previous example, providing the advantage of replacing two right angle prisms with the mirror 412. In addition, the design of FIG. 8 allows the relay optics associated with Porro prisms 414 to be replaced with magnification optics, eliminating the need for a conventional microscope body, as detailed below. Essentially, the pitch section becomes the microscope body, reducing the overall size to be about the size of a traditional microscope.

A roll section of assembly 400 includes mirror 412 and is pivotally mounted in a housing for allowing the objective lens 410 to be rotated without causing an eyepiece (not shown, but connected to right angle prisms 416) of a microscope to move. The eyepieces and microscope may be similar to those described above with other examples. In this example, the mirror 412 rotates at half the rate of the roll motion of objective lens 410 via a gear system, not shown. For instance, for 30 degrees of roll of the objective lens 410, mirror 412 would need to rotate only 15 degrees about a pivot axis represented by arrow 424. It is noted that the mirror 412 and objective lens 410 have the same axis of rotation and this axis is equidistant between and parallel to a face of each of the Porro prisms 414. The objective lens focus may operate the same as described above with other examples. Porro prisms 414 and right angle prisms 416 form a portion of a pitch section for allowing the objective lens to be moved towards and away from the eyepiece without causing the eyepiece to move about an axis represented by arrow 426. Preferably, axis 424 is orthogonal to axis 426. Essentially, the pitch section of this example may be the same as the pitch sections described above.

Figure 9:
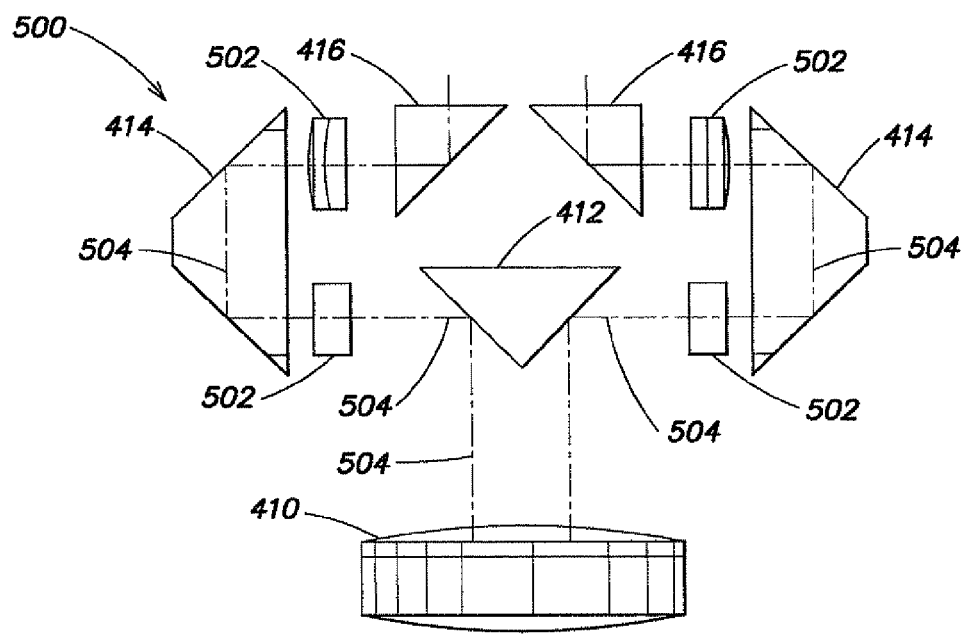
FIG. 9 is an elevation view of the optical components of still another example of the present disclosure.
Figure 10:
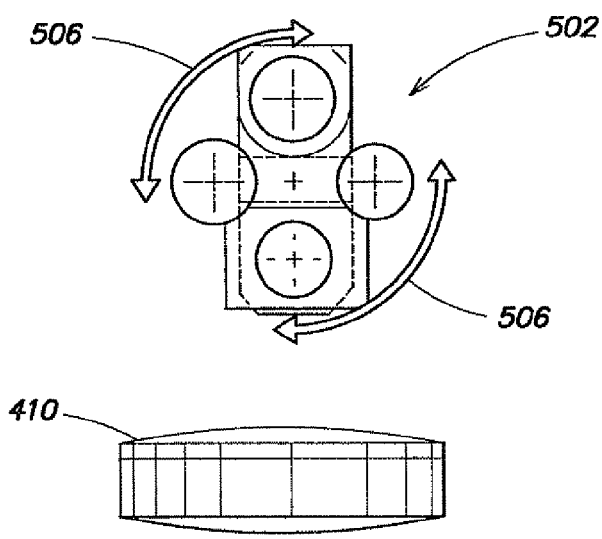
FIG. 10 is separate view of a portion of FIG. 9.

FIG. 9 is an exploded view of only the optical elements without the clutter and distraction of the mechanical elements. FIG. 9 shows an example of an objective lens assembly 500, the same as that shown in FIG. 8, with the addition of magnification optics 502 connected to the pitch section and associated with Porro prisms 414. The optical path is represented by dashed lines 504 Magnification optics 502 may include a pair of rotating lens pairs, as shown in FIG. 10, allowing for a variety of magnification powers (in this example, two different magnification ratios and four different magnification powers). If one pair of lenses has a magnification ratio of 1:2, then rotating that pair 180 degrees, as indicated by arrows 506, changes the ratio to 2:1. The right and left set of optics 502 are connected mechanically (not shown) so that when one set is rotated so is the other. The relay pairs can be Galilean or Keplerian, depending on design requirements for a microscope. As those skilled in the art will appreciate, a Galilean lens pair will provide a more compact design.

Figure 11:
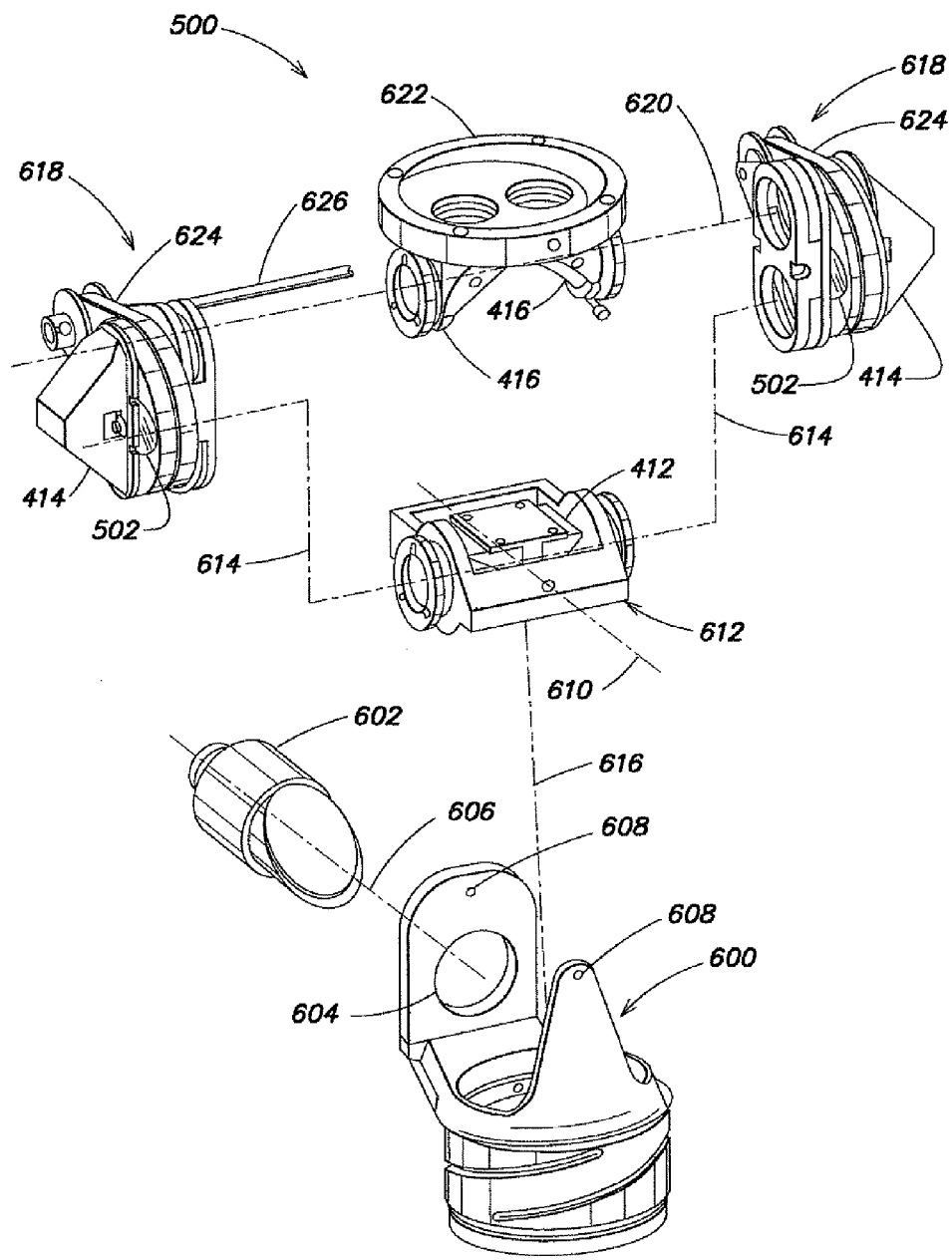
FIG. 11 is an exploded perspective view of the major components of the example of FIG. 9.

FIG. 11 shows the design of FIG. 9 in a perspective exploded view including major components; though some mechanical structure is not shown for clarity. Objective lens 410 (not shown) is held within housing 600, including any focus adjustments available. Housing 600 may also accommodate an illumination module 602 held within opening 604, as indicated by dashed line 606. Illumination module 602 may be of any construction or for any purpose required by the needs of the microscope. In addition, module 602 may be a light fiber instead of the module itself.

Housing 600 rotates in roll by a user grasping housing 600 and pivoting the housing about pivot holes 608 along axis 610. Housing 600 is pivotally connected to pivot mirror housing 612 by conventional mechanisms not shown. Also not shown are gears that preferably cause mirror 412 to pivot within mirror housing 612 at half the rate of housing 600. Mirror housing 612 pivots in pitch about axis 614. It is noted that dashed line 616 represents the field of view center point of the objective lens 410. Thus, it can be seen that mirror housing 612 connects a roll section of the lens assembly to a pitch section of the lens assembly. The roll section is comprised of the mirror 412 and the associated mechanisms shown and unshown that allow the mirror to rotate in roll without causing an eyepiece connected to the objective lens assembly to move.

Mirror housing 612 is rotatably connected to pitch assembly, shown generally at 618, including Porro prisms 414, and magnification optics 502. Pitch assembly 618 rotates about axis 614 and axis 620 and is connected to right angle prism housing 622. Prism housing 622 typically has a connector for attaching binocular units (not shown) attached for users viewing. Prism housing 622 may also have structure (not shown) for connecting the objective lens assembly 500 to a microscope support arm or stand and thereby, eliminate the need for a microscope body, typically found in the prior art. This allows for a much more compact design, which reduces spacing requirements and leads to other advantages, as those skilled in the art will appreciate. Alternatively, prism housing 622 may simply be retrofitted to attach to an existing microscope body to realize the advantages of the inventive objective lens assembly, in accordance with the present invention. Essentially, prism housing 622 may serve as an attachment mechanism for attaching the objective lens assembly 400 or 500 to a microscope, such as that shown in FIG. 3. The belts 624 cause the magnification lens pairs to rotate in unison, as they are connected by common rod 626 that is partially shown, but actually connects both magnification optics 502 together. Rod 626, in turn may be connected to a knob, motor, handle, or other mechanism for a user to rotate. Of course, magnification optics 502 are optional, and an assembly similar to FIG. 8 may be used instead, depending on design requirements, without departing from the scope of the present invention. The examples of FIGS. 8-11 conveniently allow a user to move the field of view, where the objective lens assembly is grasped by a user and manually moved to a desired field of interest in pitch and roll without causing a viewing unit to move. This is a simple, compact, inexpensive (compared to the prior art) design that provides a user a much improved viewing experience compared to the prior art.

Thus, has been shown, an objective lens assembly and a microscope that allows the objective lens to be rotated in pitch and roll without causing the eyepieces to move. By implementing any or all of the teachings described above, a number of benefits and advantages can be attained including improved reliability, reduced surgical time, increased efficiency, and production of higher quality recorded images during movement of the objective lens because of the independent movement relative to the viewing unit that is held stable by the support structure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

I claim:

1. An objective lens assembly for attachment to a surgical microscope comprising:
    an objective lens;
    a roll section for allowing the objective lens to be rotated about a first axis without causing a pair of eyepieces of the microscope to move wherein the roll section may be rotated by a user in a direction of a field of interest;
    a pitch section for allowing the objective lens to be rotated about a second axis orthogonal to the first axis without causing the pair of eyepieces to move wherein the pitch section may be rotated by a user in the direction of the field of interest;
    an attachment mechanism for attaching the objective lens assembly to the microscope; and
    wherein the objective lens assembly is moved to the field of interest by a user grasping and moving the objective lens assembly in the direction of the field of interest.

2. The objective lens assembly of claim 1 further including a fine focus mechanism.

3. The objective lens assembly of claim 1 further including an illumination module.

4. The objective lens assembly of claim 1, wherein the roll section rotates sideways with respect to the pitch section and includes a ninety degree minor that rotates as the roll section rotates for directing light towards the pair of eyepieces.

5. The objective lens assembly of claim 1, wherein the roll section rotates sideways with respect to the pitch section and includes at least a pair of prisms that rotate in unison for directing light towards the pair of eyepieces.

6. The objective lens assembly of claim 1, wherein the roll section includes the objective lens.

7. The objective lens assembly of claim 1, wherein the roll section includes an illumination module for illuminating an area being viewed by the microscope.

8. The objective lens assembly of claim 1, wherein the objective lens includes a fine focus mechanism.

9. The objective lens assembly of claim 1, wherein the pitch section rotates about an axis perpendicular with respect to the roll section.

10. The objective lens assembly of claim 1, wherein the pitch section is a type of inclinable binocular unit.

11. The objective lens assembly of claim 1, wherein the pitch section includes the attachment mechanism.

12. A surgical microscope comprising: a viewing unit through which a user views a field of interest; a microscope body cooperatively attached to the viewing unit; support structure connected to the microscope body for supporting and positioning the microscope in a desired position including a support arm pivotally connected to the microscope body; and an objective lens assembly attached to the microscope body including, an objective lens; a roll section for allowing the objective lens to be rotated about a first axis without causing the viewing unit of the microscope to move wherein the roll section may be rotated by a user in a direction of a field of interest; a pitch section for allowing the objective lens to be rotated about a second axis orthogonal to the first axis without causing the viewing unit to move wherein the pitch section may be rotated by a user in the direction of the field of interest; and wherein the objective lens assembly is moved to view the field of interest by a user grasping and moving the objective lens assembly in the direction of the field of interest.

13. The microscope of claim 12, wherein the viewing unit includes a pair of eyepieces and an inclinable binocular unit.

14. The microscope of claim 12, wherein the viewing unit includes a pair of eyepieces.

15. The microscope of claim 12, wherein the viewing unit includes a beam-splitter and a connector for attaching additional viewing units or optical recording devices.

16. The microscope of claim 12, wherein the support structure includes multiple arms that are rotatable about different axes for initially positioning the microscope.

17. The microscope of claim 12, wherein the support structure is mounted on a wheeled base to allow the microscope to be easily moved.

18. The microscope of claim 12, wherein the support structure includes a power or illumination source.

19. The objective lens assembly of claim 12 further including a fine focus mechanism.

20. The objective lens assembly of claim 12 further including an illumination module.

21. The objective lens assembly of claim 12, wherein the roll section rotates sideways with respect to the pitch section and includes a ninety degree minor that rotates as the roll section rotates for directing light towards the pair of eyepieces.

22. The objective lens assembly of claim 12, wherein the roll section rotates sideways with respect to the pitch section and includes at least a pair of prisms that rotate in unison for directing light towards the eyepiece.

23. The objective lens assembly of claim 12, wherein the roll section includes the objective lens.

24. The objective lens assembly of claim 12, wherein the roll section includes an illumination module for illuminating an area being viewed by the microscope.

25. The objective lens assembly of claim 12, wherein the objective lens includes a fine focus mechanism.

26. The objective lens assembly of claim 12, wherein the pitch section rotates about an axis perpendicular with respect to the roll section.

27. The objective lens assembly of claim 12, wherein the pitch section is a type of inclinable binocular unit.

28. The objective lens assembly of claim 12, wherein the pitch section includes the attachment mechanism.

29. A surgical microscope comprising: a viewing unit including a pair of eyepieces, through which a user views a field of interest; a microscope body cooperatively attached to the viewing unit; support structure including multiple support arms connected to the microscope body for supporting and positioning the microscope in a desired position including one of the multiple support arms pivotally connected to the microscope body; and an objective lens assembly attached to the microscope body including, an objective lens, including a fine focus mechanism; a roll section incorporating the objective lens and including a pair of prisms for allowing the objective lens to be rotated about a first axis without causing the viewing unit of the microscope to move wherein the roll section may be rotated by a user in a direction of a field of interest; a pitch section including a type of inclinable binocular unit for allowing the pitch section to rotate about an axis perpendicular with respect to the roll section thereby allowing the objective lens to be moved about a second axis orthogonal to the first axis without causing the viewing unit to move wherein the pitch section may be rotated by a user in the direction of the field of interest; and wherein the objective lens assembly is moved to view the field of interest by a user grasping and moving the objective lens assembly in the direction of the field of interest.

30. The microscope of claim 29, wherein the viewing unit includes a beam-splitter and a connector for attaching additional viewing units or optical recording devices.

31. The microscope of claim 29, wherein the multiple arms are rotatable about different axes for initially positioning the microscope.

32. The microscope of claim 29, wherein the support structure is mounted on a wheeled base to allow the microscope to be easily moved.

33. The microscope of claim 29, wherein the objective lens assembly further includes an illumination module.

34. The microscope of claim 29, wherein the illumination module is connected to the roll section.

35. A method of using a surgical microscope including a viewing unit having a pair of eyepieces through which a user views a field of interest, a microscope body cooperatively attached to the viewing unit, support structure including multiple support arms connected to the microscope body for supporting and positioning the microscope in a desired position including one of the multiple support arms pivotally connected to the microscope body, the method comprising the steps of: attaching an objective lens assembly to the microscope body, the objective lens assembly including, an objective lens having a fine focus mechanism, a roll section attached to the objective lens and including a ninety degree mirror for allowing the objective lens to be rotated about a first axis without causing the viewing unit of the microscope to move, and a pitch section attached to the roll section including an inclinable binocular unit for allowing the pitch section to rotate about an axis perpendicular with respect to the roll section thereby allowing the objective lens to be moved about a second axis orthogonal to the first axis without causing the viewing unit to move, and a user directing the objective lens assembly to view the field of interest by grasping and moving the objective lens assembly in the direction of the field of interest.

36. The method of claim 35, wherein a pair of prisms are substituted to replace the ninety degree mirror.

37. An objective lens assembly comprising: an objective lens; a roll section attached to the objective lens, the roll section including a right angle mirror that rotates at a rate half as much as the objective lens rotates when the objective lens assembly is rotated in a roll axis by the user; a pitch section attached to the roll section and rotatable about a first axis orthogonal to the roll axis such that the objective lens rotates about a second axis orthogonal to the first axis when the objective lens assembly is rotated about the pitch axis by the user; and wherein the objective lens assembly may be grasped by a user and manually moved to a desired field of interest in pitch and roll without causing the viewing unit to move.

38. The objective lens assembly of claim 37 further including magnification optics connected to the pitch section, wherein the magnification optics include rotatable lens pairs for providing a variety of magnification powers.

39. A surgical microscope comprising: a viewing unit through which a user views a field of interest; and an objective lens assembly including a housing, the objective lens assembly further including; an objective lens attached to the housing; a roll section pivotally connected to the housing for allowing the objective lens to be rotated about a first axis without causing the viewing unit of the microscope to move wherein the roll section may be rotated by a user in a direction of a field of interest; a pitch section rotatable with respect to the housing and the roll section for allowing the objective lens to be rotated about a second axis orthogonal to the first axis without causing the viewing unit to move wherein the pitch section may be rotated by a user in the direction of the field of interest; wherein the housing may be attached to a support arm or other structure, thereby eliminating the need for a microscope body; and wherein the objective lens assembly is moved to view the field of interest by a user grasping and moving the objective lens assembly in the direction of the field of interest.

* * * * *